(12) United States Patent
Oshikawa et al.

(10) Patent No.: US 12,394,025 B2
(45) Date of Patent: Aug. 19, 2025

(54) IMAGE GENERATION DEVICE, IMAGE GENERATION METHOD, AND LEARNED MODEL GENERATION METHOD

(71) Applicant: Shimadzu Corporation, Kyoto (JP)

(72) Inventors: Shota Oshikawa, Kyoto (JP); Wataru Takahashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 609 days.

(21) Appl. No.: 17/281,781

(22) PCT Filed: Sep. 27, 2019

(86) PCT No.: PCT/JP2019/038168
§ 371 (c)(1),
(2) Date: Mar. 31, 2021

(87) PCT Pub. No.: WO2020/075531
PCT Pub. Date: Apr. 16, 2020

(65) Prior Publication Data
US 2021/0398254 A1 Dec. 23, 2021

(30) Foreign Application Priority Data

Oct. 10, 2018 (JP) .................. 2018-191880

(51) Int. Cl.
*G06T 5/73* (2024.01)
*G06F 18/214* (2023.01)
*G06N 20/00* (2019.01)

(52) U.S. Cl.
CPC .............. *G06T 5/73* (2024.01); *G06F 18/214* (2023.01); *G06N 20/00* (2019.01);
(Continued)

(58) Field of Classification Search
CPC ........... G06T 5/003; G06T 2207/10081; G06T 2207/20081; G06T 2207/30008; G06T 2207/30101; G06N 20/00; G06F 18/214
See application file for complete search history.

(56) References Cited

U.S. PATENT DOCUMENTS

| | | | |
|---|---|---|---|
| 2005/0100208 A1* | 5/2005 | Suzuki | G06T 5/30 |
| | | | 382/128 |
| 2009/0169075 A1 | 7/2009 | Ishida et al. | |
| 2014/0328524 A1* | 11/2014 | Hu | G06T 7/174 |
| | | | 382/128 |

FOREIGN PATENT DOCUMENTS

WO 2007/029467 A1 3/2007

OTHER PUBLICATIONS

ImgAug (http://web.archive.org/web/20180915213100/https://github.com/aleju/imgaug) (Year: 2018).*
(Continued)

*Primary Examiner* — Mark Roz
(74) *Attorney, Agent, or Firm* — Muir Patent Law, PLLC (57) ABSTRACT

This image generation device is provided with: a learning image generation unit (1) for generating a training input image and a training output image based on three-dimensional data; a noise addition unit (2) for adding the same noise to the training input image and the training output image; a learning unit (3) for learning a learning model for extracting or removing a specific portion by performing machine learning based on the training input image to which the noise has been added and the training output image to which the noise has been added; and an image generation unit (4) for generating an image from which the specific portion has been extracted or removed by using a learned learning model.

7 Claims, 5 Drawing Sheets

(52) U.S. Cl.
CPC ............... *G06T 2207/10081* (2013.01); *G06T 2207/20081* (2013.01); *G06T 2207/30008* (2013.01); *G06T 2207/30101* (2013.01)

(56) References Cited

OTHER PUBLICATIONS

Lyra, MATLAB as a Tool in Nuclear Medicine Image Processing, MATLAB 2011 (Year: 2011).*
Written Opinion for PCT application No. PCT/JP2019/038168 dated Nov. 26, 2019, submitted with a machine translation.

* cited by examiner

IMAGE GENERATION DEVICE, IMAGE GENERATION METHOD, AND LEARNED MODEL GENERATION METHOD

TECHNICAL FIELD

The present invention relates to an image generation device, an image generation method, and a learned model generation method.

BACKGROUND ART

Conventionally, an image generation device is known. An image generation device is disclosed, for example, in WO 2007/029467.

The above-described WO 2007/029467 discloses an image processing apparatus (image generation device) in which machine learning is performed based on a training input image and a training output image and an enhanced image is output from a processing target image by using the learned result. In this image processing apparatus, a plurality of training input images is generated by applying a plurality of image processing to a training input image in order to learn many patterns. For example, the processing is performed so that the image quality of the training input image becomes coarse. In this case, noise is included in the training input image, and the learning result for reducing the noise is acquired by machine learning.

PRIOR ART DOCUMENT

Patent Document

Patent Document 1: WO 2007/029467

SUMMARY OF THE INVENTION

Problems to be Solved by the Invention

However, in the image processing apparatus of the above-described WO 2007/029467, in order to perform the machine learning of reducing noise in the training input image, a filter for extracting the low-frequency area of the image for smoothing the noise is learned. Therefore, when generating an image using the learned result, there is a problem that the image is smoothed and the output image is blurred.

The present invention has been made to solve the above-described problems. An object of the present invention is to provide an image generation device, an image generation method, and a learned model generation method capable of suppressing blurring when generating an image using a learning model learned by machine learning.

Means for Solving the Problem

In order to attain the above-described object, the image generation device according to the first aspect of the present invention, include:

- a learning image generation unit configured to generate, based on three-dimensional data having three-dimensional pixel value data, a two-dimensional training input image in an area including a specific portion of a subject and a training output image that is an image showing the specific portion or an image excluding the specific portion at the same angle of view as the training input image;
- a noise addition unit configured to add the same noise to the training input image and the training output image;
- a learning unit configured to learn a learning model for extracting or removing the specific portion by performing machine learning based on the training input image to which the noise has been added and the training output image to which the noise has been added; and
- an image generation unit configured to generate, from a captured image including the specific portion, an image from which the specific portion has been extracted or removed, using a learned learning model.

In the image generation device according to the first aspect of the present invention, with the above-described configuration, the same noise is added to both the training input image and the training output image. Therefore, the image processing for extracting or removing a specific portion which is a difference between the training input image and the training output image other than the noise component can be learned. As a result, since a filter for smoothing the noise is not learned, it is possible to suppress the blurring of an image to be generated.

In the image generation device according to the first aspect of the present invention, preferably, the learning image generation unit is configured to acquire the three-dimensional data based on a computed tomography image that captured the subject and generate the training input image and the training output image by a digital reconstruction simulation. With this configuration, a plurality of sets of the training input image and the training output image can be easily generated from a computed tomography image by a digital reconstruction simulation, so that machine learning can be performed using the plurality of sets. As a result, it is possible to improve the learning accuracy of the learning model.

In the image generation device according to the first aspect of the present invention, preferably, the noise addition unit is configured to add noise adjusted based on noise of an imaging result that captured an image to the training input image and the training output image. With this configuration, since it is possible to perform the machine learning by adding noise corresponding to the noise at the time of the actual imaging to the training input image and the training output image, it is possible to effectively suppress the noise effect when generating an image from an image including the imaged specific portion by using the learned learning model and extract or remove the specific portion.

In this case, preferably, the noise addition unit is configured to add Gaussian noise and is configured to add Gaussian noise adjusted to a standard deviation corresponding to a standard deviation of noise of the imaging result that captured the image to the training input image and the training output image. With this configuration, the standard deviation of the Gaussian noise to be added can be adjusted to the noise of the image to be actually captured, so that the specific portion can be extracted or removed by more effectively suppressing the effect of the noise on the image generation.

In the image generation device according to the first aspect of the present invention, preferably, the specific portion is a bone, the learning image generation unit is configured to generate a two-dimensional training input image in an area including a bone of the subject and the training output image excluding the bone of the subject, the learning unit is configured to learn the learning model for removing the bone by performing machine learning based on the training input image to which the noise has been added and the training output image to which the noise has been added, and the image generation unit is configured to generate, from the image including the imaged bone, an image from which the bone has been removed using the learned learning model. With this configuration, since it is possible to learn the learning model for removing only a bone without removing the noise component as much as possible. Thus, it is possible to output a bone suppression image in which blurring is suppressed by generating an image using the learning model.

In the image generation device according to the first aspect of the present invention, preferably, the specific portion is a blood vessel, the learning image generation unit is configured to generate a two-dimensional training input image of an area including a blood vessel of the subject and the training output image indicating the blood vessel of the subject, the learning unit is configured to learn the learning model for extracting the blood vessel by performing machine learning, based on the training input image to which the noise has been added and the training output image to which the noise has been added, and the image generation unit is configured to generate, from an image including an imaged blood vessel, an image by extracting the blood vessel using the learned learning model. With this configuration, since it is possible to learn the learning model for extracting a blood vessel without removing the noise component as much as possible, it is possible to output a blood vessel image in which blurring is suppressed by generating an image using the learning model.

An image generation method according to a second aspect of the present invention includes:
generating a two-dimensional training input image in an area including a specific portion of a subject, based on three-dimensional data having three-dimensional pixel value data;
generating a training output image which is an image showing the specific portion or an image excluding the specific portion at the same angle of view as the training input image;
adding the same noise to the training input image and the training output image;
learning a learning model for extracting or removing the specific portion by performing machine learning based on the training input image to which the noise has been added and the training output image to which the noise has been added; and generating an image from which the specific portion has been extracted or removed, from the captured image including the specific portion, using the learned learning model.

In the image generation method according to the second aspect of the present invention, with the above-described configuration, since the same noise is added to both the training input image and the training output image, it is possible to learn the image processing for extracting or removing the specific portion which is a difference between the training input image and the training output image other than the noise component. As a result, since the filter for smoothing noise is not learned, the blurring of the image to be generated can be suppressed.

In a learned model generation method according to a third second aspect of the present invention, a method of producing a learned model, includes:
generating a two-dimensional training input image in an area including the specific portion of a subject, based on three-dimensional data having three-dimensional pixel value data;
generating a training output image which is an image showing the specific portion or an image excluding the specific portion at the same angle of view as the training input image;
adding the same noise to the training input image and the training output image; and
learning a learning model for extracting or removing the specific portion by performing machine learning based on the training input image to which the noise has been added and the training output image to which the noise has been added.

In the learned model production method according to the third aspect of the present invention, by configuring as described above, since the same noise is added to both the training input image and the training output image, it is possible to learn the image processing for extracting or removing the specific portion which is a difference between the training input image and the training output image other than the noise component. As a result, since a filter for smoothing noise is not learned, the blurring of an image to be generated can be suppressed.

Effects of the Invention

According to the present invention, as described above, it is possible to suppress blurring when generating an image by using the learning model learned by machine learning.

EMBODIMENTS FOR CARRYING OUT THE INVENTION

Hereinafter, embodiments in which the present invention is embodied will be described with reference to the attached drawings.

Referring to FIG. 1 to FIG. 8, the configuration of an image generation device 100 according to one embodiment of the present invention, an image generation method of one embodiment, and a generation method of a learned model according to one embodiment will be described.
(Configuration of Image Processing Device)

Figure 1:
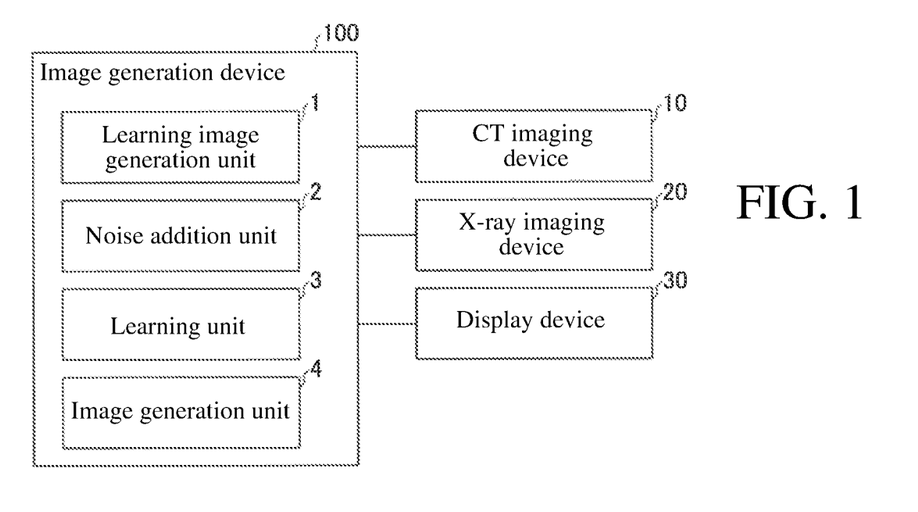
FIG. 1 is a block diagram showing an image generation device according to one embodiment.

First, referring to FIG. 1, the configuration of the image generation device 100 according to a first embodiment will be described.

The image generation device 100 is configured to generate an image of the X-ray image from which a specific portion has been extracted or removed, using a learned learning model by machine learning. As shown in FIG. 1, the image generation device 100 is provided with a learning image generation unit 1, a noise addition unit 2, a learning unit 3, and an image generation unit 4. Further, the image generation device 100 is configured to acquire a CT image from a CT imaging device 10. Further, the image generation device 100 is configured to acquire an X-ray image from the X-ray imaging device 20. The image generation device 100 is configured to transmit the generated image to a display device 30.

The image generation device 100 is provided with a communication unit for acquiring data from the CT imaging device 10 or the X-ray imaging device 20 and for transmitting the data to the display device 30. The communication unit includes, for example, an input/output interface, such as, e.g., an HDMI (Registered Trade Mark) (High-Definition Multimedia Interface), a Display Port, and a USB port.

Further, the image generation device 100 includes, for example, a CPU (Central Processing Unit), a GPU (Graphics Processing Unit), a ROM (Read Only Memory), and a RAM (Random Access Memory) as hardware configuration. The image generation device 100 includes, as a storage unit, an HDD (Hard Disk Drive), a non-volatile memory, and the like.

Figure 2:
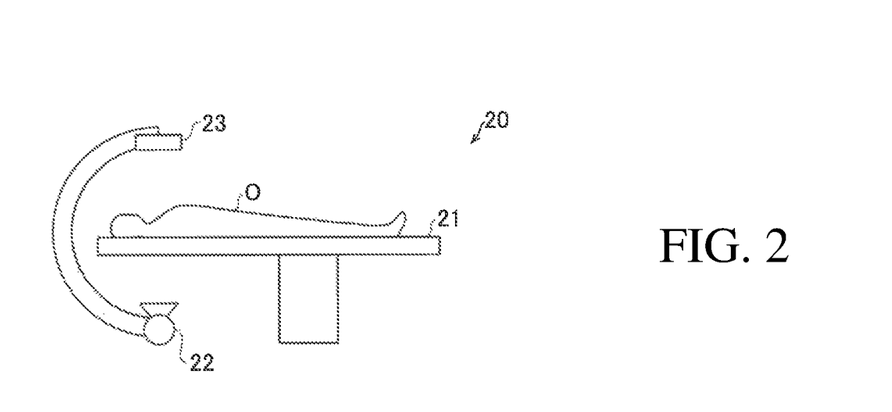
FIG. 2 is a diagram showing an X-ray imaging device for capturing an image for generating an image by the image generation device according to an embodiment.

The X-ray imaging device 20 includes, as shown in FIG. 2, a top board 21, an X-ray irradiation unit 22, and an FPD (Flat Panel Detector) 23. The top board 21 is configured to support a subject O (person). The X-ray irradiation unit 22 is configured to emit X-rays toward the subject O. The FPD 23 is configured to detect the X-rays emitted from the X-ray irradiation unit 22 and transmitted through the subject O.

The learning image generation unit 1 of the image generation device 100 is configured to generate a training input image and a training output image for learning a learning model by the learning unit 3. Specifically, the learning image generation unit 1 generates, based on three-dimensional data having three-dimensional pixel value data, a two-dimensional training input image of an area including a specific portion of the subject O and a training output image which is an image showing the specific portion or an image excluding the specific portion at the same angle of view of the training input image. More specifically, the learning image generation unit 1 acquires three-dimensional data (data having a three-dimensional voxel value), based on a computed tomography image (CT image) that captured the subject O. The learning image generation unit 1 is configured to generate the training input image and the training output image by a digital reconstruction simulation (DRR) based on three-dimensional data.

Further, the learning image generation unit 1 is configured to generate a plurality of sets of the training input image and the training output image from single three-dimensional data (CT image data). For example, the learning image generation unit 1 is configured to generate as many as about 100,000 sets of the training input image and the training output image from single three-dimensional data. The learning image generation unit 1 is configured to generate a plurality of sets of the training input image and the training output image with different projection angles, projection coordinates, and parameters for generating a DRR image, contrasts, edge-enhancement, etc., at digital reconstruction simulation.

Figure 4:
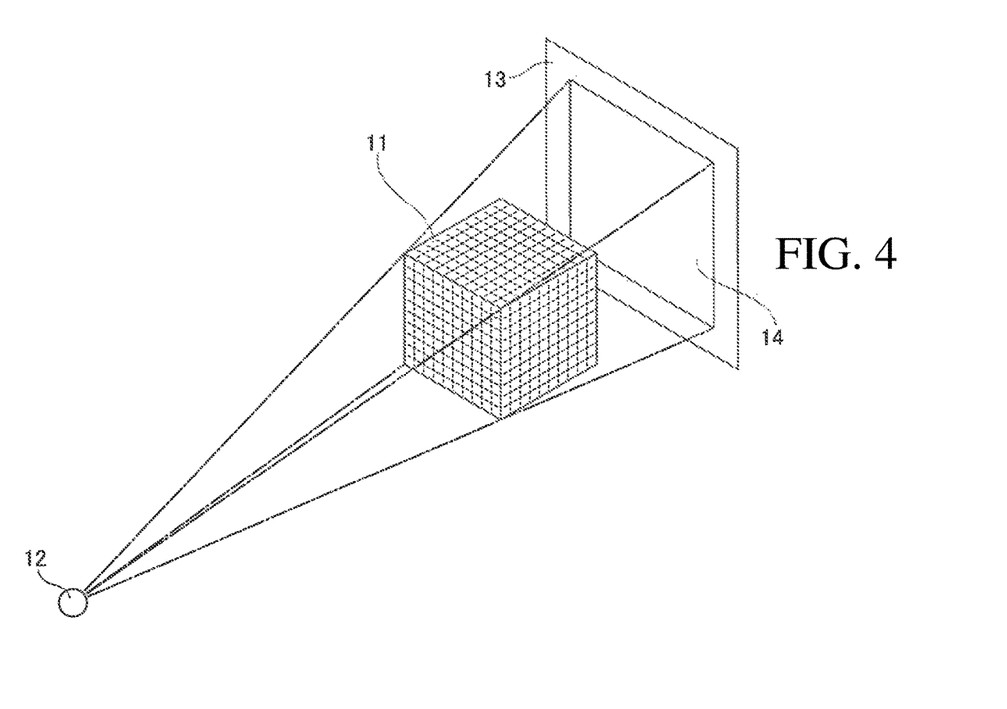
FIG. 4 is a diagram for explaining a learning image generation method according to an embodiment.

As shown in FIG. 4, when generating an image by a digital reconstruction simulation, the three-dimensional data 11, the X-ray source 12, and the projection plane 13 are arranged virtually, the learning image generation unit 1 performs a virtual projection with respect to the three-dimensional data 11. Then, the learning image generation unit 1 generates the image 14 projected on the projection plane 13 by calculation based on the three-dimensional data 11.

When generating the training input image, the learning image generation unit 1 calculates each pixel value of the two-dimensional image 14 by virtually emitting X-rays from the X-ray source 12 to the portion of the three-dimensional data 11 including a specific portion and adding the CT value (voxel value) passing therethrough.

Further, when generating the training output image, the learning image generation unit 1 calculates each pixel value of the two-dimensional image 14 by virtually emitting X-rays from the X-ray source 12 to the portion of the three-dimensional data 11 including a specific portion and adding only the CT value (voxel value) of the specific portion or excluding the CT value (voxel value) of the specific portion. For example, when extracting the specific portion, each pixel value of the two-dimensional image 14 is calculated by adding only the CT value (voxel value) in the range corresponding to the specific portion. When extracting the specific portion on the CT, a known 3D segmentation technique may be used, or a specific portion area may be acquired from treatment plan data generated by a treatment plan device. When excluding a specific portion, each pixel value of the two-dimensional image 14 is calculated by adding excluding the CT value (voxel value) in the range corresponding to the specific portion.

Further, in a case where a moving (pulsating) part such as a blood vessel is set as a specific portion, the learning image generation unit 1 is configured to generate a training input image and a training output image, based on four-dimensional data including time in a three-dimensional space. With this configuration, it is possible to perform learning with high accuracy even in the case of an object that moves with time.

The noise addition unit 2 is configured to add noise to the training input image and the training output image generated by the learning image generation unit 1. Here, in this embodiment, the noise addition unit 2 is configured to add the same noise to the training input image and the training output image. The noise addition unit 2 is configured to add the noise adjusted based on the noise of the imaging result that captured the image to the training input image and the training output image. That is, the noise addition unit 2 is configured to add the noise adjusted based on the noise included at the time of the X-ray imaging. The noise by the X-ray imaging by the X-ray imaging device 20 is measured, for example, by X-ray imaging with a uniform material (e.g., a material having substantially equal X-ray transmittance (e.g., air, water)) disposed between the X-ray irradiation unit 22 and the FPD 23.

The noise addition unit 2 is configured to add Gaussian noise. Further, the noise addition unit 2 is configured to add Gaussian noise adjusted to a standard deviation σ corresponding to a standard deviation σ of the noise of the imaging result that captured the image to the training input image and the training output image. That is, the noise addition unit 2 is configured to add, by the X-ray imaging device 20, the Gaussian noise adjusted to the equivalent standard deviation σ based on the noise included when the X-ray imaging was performed.

The noise addition unit 2 is configured to add the same noise to a set of the training input image and the training output image generated under the same condition. On the other hand, the noise addition unit 2 is configured to add a different noise for each set of the training input image and the training output image to be generated. For example, the noise addition unit 2 is configured to add the noise while randomly changing the parameter for each set of the training input image and the training output image to be generated.

Figure 3:
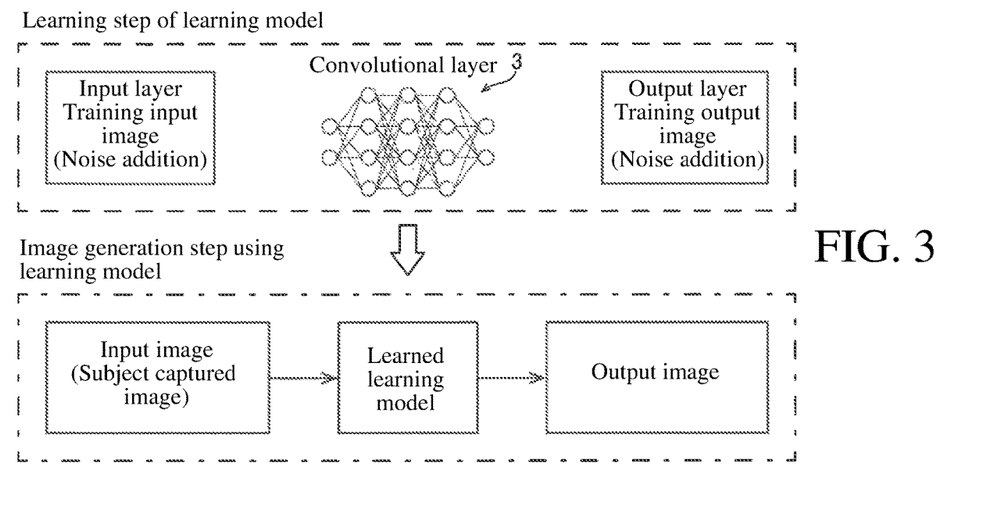
FIG. 3 is a diagram for explaining a learning method and a learning image generation method according to an embodiment.

In this embodiment, as shown in FIG. 3, the learning unit 3 is configured to learn a learning model for extracting or removing a specific portion by performing machine learning based on the training input image to which noise has been added and the training output image to which noise has been added. The learning unit 3 is configured to perform the image analysis based on the training input image to which the noise has been added and the training output image to which the noise has been added by AI (Artificial Intelligence). The learning unit 3 is configured to perform learning using a convolutional layer. The learning unit 3 is configured to perform the learning by deep learning. The learning unit 3 is configured to perform the learning using a neural network.

Note that the learning of the learning model by the learning unit 3 may be performed for each subject O or for each X-ray imaging device 20. Further, the learning may be performed periodically. Alternatively, the learning model may be generated in which the learning data of different subjects O is integrated.

In this embodiment, as shown in FIG. 3, the image generation unit 4 is configured to generate an image from which the specific portion has been extracted or removed from the image including the captured specific portion by using the learned learning model. That is, the image generation unit 4 is configured to generate a two-dimensional image from which the specific portion has been extracted or removed, from the two-dimensional X-ray image including the specific portion imaged by the X-ray imaging device 20 using the learning model learned by the learning unit 3. Further, the image generation unit 4 is configured to generate an image from which the specific portion has been extracted or removed, from the real-time two-dimensional image captured by the X-ray imaging device 20. For example, the image generation unit 4 produces an image from which a bone has been removed, a blood vessel has been extracted, or an instrument such as a stent has been extracted, from the image fluoroscopically viewed using the X-ray imaging device 20, for example, during the treatment of the subject O. The image generation unit 4 transmits the generated image to the display device 30. As a result, the image from which the specific portion has been extracted or removed is displayed on the display device 30.

Figure 5:
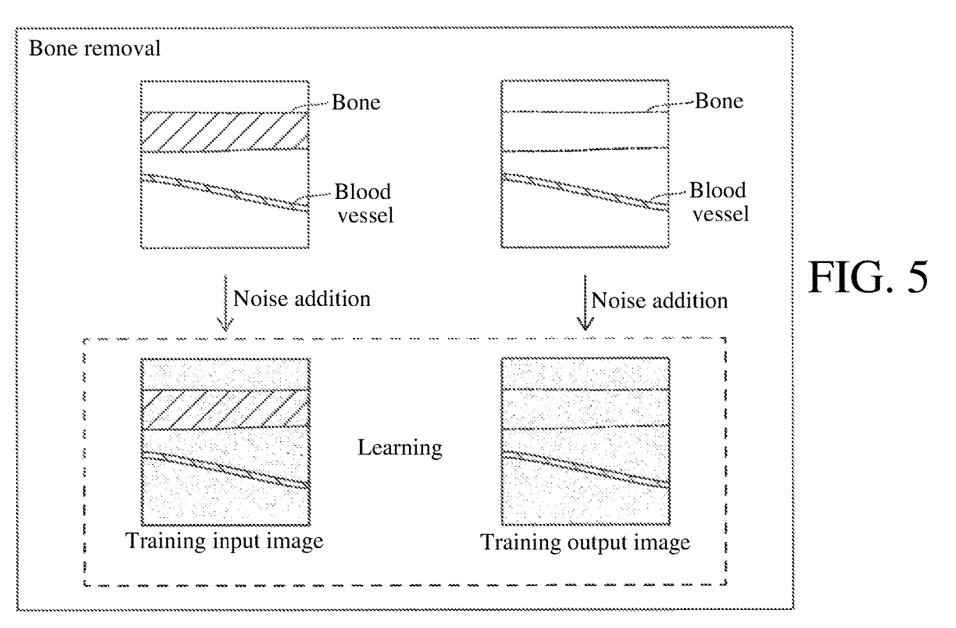
FIG. 5 is a diagram for explaining a learning method when removing a bone according to an embodiment.

Referring to FIG. 5, an example in which the specific portion is a bone will be described. As shown in FIG. 5, a two-dimensional training input image of the area including a bone of a subject O which is a specific portion is produced by the learning image generation unit 1. Further, a two-dimensional training output image excluding a bone of a subject O, which is a specific portion, is generated by the learning image generation unit 1. Then, the noise addition unit 2 adds the same noise to the two-dimensional training input image and training output image. A learning model for removing the bone by machine learning from the training input image and the training output image to which the same noise has been added is learned by the learning unit 3. Then, using the learning model for removing the bone, an image from which the bone has been removed from the X-ray image of the subject O captured by the X-ray imaging device 20 is generated by the image generation unit 4.

Figure 6:
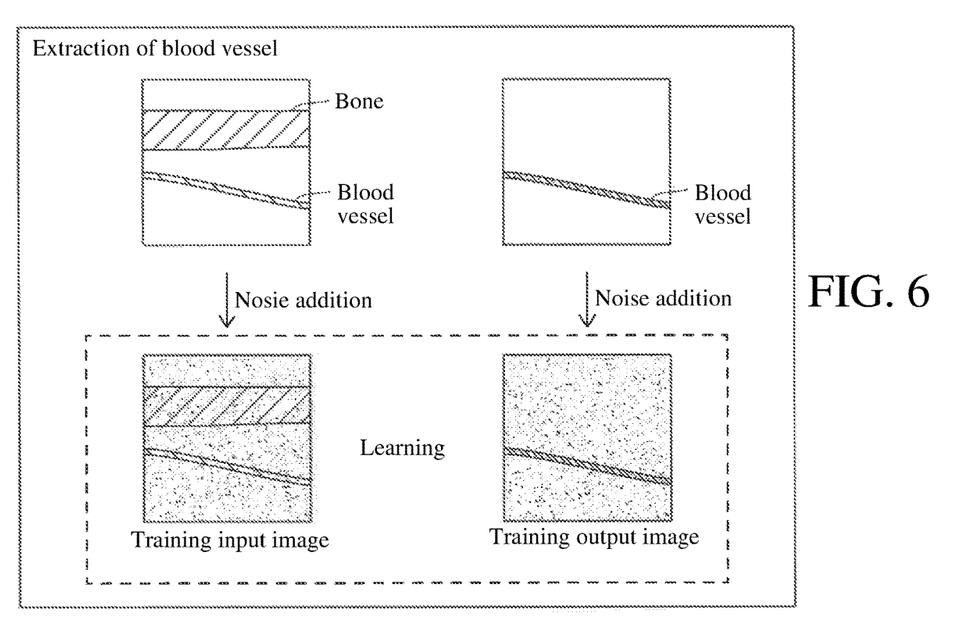
FIG. 6 is a diagram for explaining a learning method when extracting a blood vessel according to an embodiment.

Referring to FIG. 6, an example in which the specific portion is a blood vessel will be described. As shown in FIG. 6, a two-dimensional training input image of the area including a blood vessel of a subject O, which is a specific portion, is generated by the learning image generation unit 1. Further, by the learning image generation unit 1, a two-dimensional training output image from which the blood vessel of the subject O, which is the specific portion, has been extracted, is generated. Then, the noise addition unit 2 adds the same noise to the two-dimensional training input image and training output image. By the learning unit 3, a learning model for extracting the blood vessel by machine learning from the training input image and the training output image to which the same noise has been added is generated by the learning image generation unit 1 are leaned. Then, using the learning model for extracting the blood vessel, an image from which the blood vessel has been extracted from the X-ray image of the subject O captured by the X-ray imaging device 20 is generated by the image generation unit 4.

(Learning Model Learning Processing)

Figure 7:
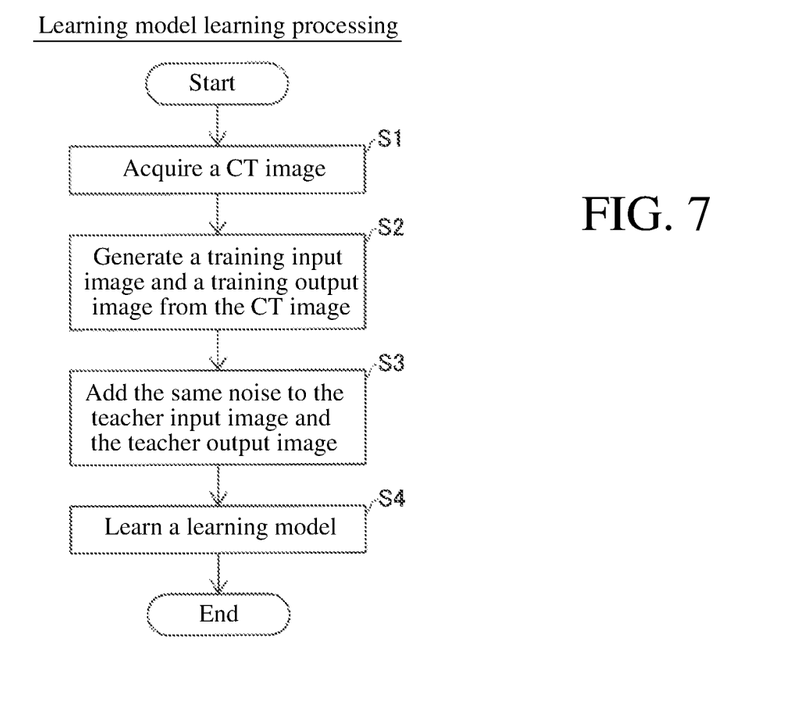
FIG. 7 is a flowchart for explaining the learning processing of a learning model according to one embodiment.

Next, referring to FIG. 7, the learning model learning processing performed by the image generation device 100 will be described.

In Step S1, a CT image (three-dimensional data) generated by the CT imaging device 10 is acquired. In Step S2, a plurality of sets of the training input image and the training output image is generated from the CT image.

In Step S3, the same noise is added to the same set of the training input image and the training output image generated. In Step S4, a learning model is learned. This generates a learned model for extracting or removing a specific portion.

(Image Generation Processing)

Figure 8:
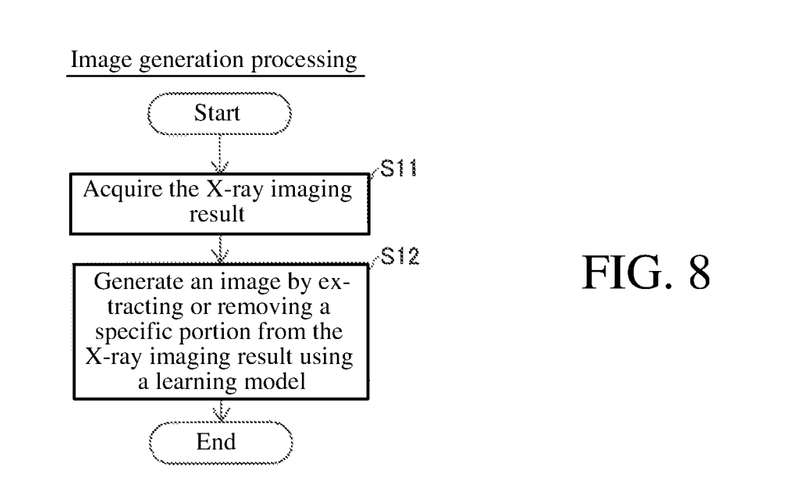
FIG. 8 is a flowchart for explaining the image generation processing according to an embodiment.

Next, referring to FIG. 8, the image generation processing by the image generation device 100 will be described.

In Step S11, the imaging result (two-dimensional X-ray image) of the subject O by the X-ray imaging device 20 is acquired. In Step S12, from the acquired X-ray image, an image from which the specific portion has been extracted or removed using the learned model is generated.

Effects of This Embodiment

In this embodiment, the following effects can be obtained.

In this embodiment, as described above, it is provided with the noise addition unit 2 for adding the same noise to the training input image and the training output image and the learning unit 3 for learning the learning model for extracting or removing the specific portion by performing machine learning based on the training input image to which the above noise has been added and the training output image to which the above noise has been added. With this, the same noise is added to both the training input image and the training output image, it is possible to learn the image processing for extracting or removing the specific portion which is a difference between the training input image and the training output image other than the noise component. As a result, since a filter for smoothing the noise is not learned, blurring of an image to be generated can be suppressed.

Further, in this embodiment, as described above, the learning image generation unit 1 is configured to acquire three-dimensional data based on the computed tomography image obtained by imaging the subject O and generate a training input image and a training output image by a digital reconstruction simulation. As a result, a plurality of sets of the training input image and the training output image can be easily generated from a computed tomography image by a digital reconstruction simulation. Therefore, machine learning can be performed using the plurality of sets. With this, it is possible to improve the learning accuracy of the learning model.

Further, in this embodiment, as described above, the noise addition unit 2 is configured to add the noise adjusted based on the noise of imaging result that captured the image to the training input image and the training output image. As a result, it is possible to perform machine learning by adding the noise corresponding to the noise in the actual imaging to the training input image and the training output image. Thus, when generating an image using the learned learning model from the image including the imaged specific portion, it is possible to extract or remove the specific portion by effectively suppressing the influence of the noise.

Further, in this embodiment, as described above, the noise addition unit 2 is configured to add the Gaussian noise and add the Gaussian noise adjusted to a standard deviation corresponding to the standard deviation of the noise of the imaging result that captured the image to the training input image and the training output image. With this, the standard deviation of the Gaussian noise to be added can be matched to the noise of the actual image to be captured. Thus, it is possible to extract or remove the specific portion while more effectively suppressing the impact of the noise on the image generation.

Further, in this embodiment, as described above, the learning image generation unit 1 is configured to generate a two-dimensional training input image of the area including a bone of a subject O and a training output image excluding the bone of the subject. Further, the learning unit 3 is configured to learn the learning model for removing a bone by performing machine learning based on training the input image to which the noise has been added and the training output image to which the noise has been added. Further, the image generation unit 4 is configured to generate an image from which a bone has been removed using the learned learning model from the image including the imaged bone. As a result, it is possible to perform learning of removing only a bone without removing the noise component as much as possible. Therefore, it is possible to output a bone suppression image in which blurring has been suppressed by generating an image using the learning model.

Further, in this embodiment, as described above, the learning image generation unit 1 is configured to generate a two-dimensional training input image of the area including a blood vessel of a subject O and a training output image indicating a blood vessel of a subject. Further, the learning unit 3 is configured to perform learning the learning model for extracting a blood vessel by performing machine learning based on the training input image to which noise has been added and the training output image to which noise has been added. Further, the image generation unit 4 is configured to generated an image by extracting a blood vessel using the learned learning model from the image including the imaged blood vessel. With this, a learning model for extracting a blood vessel can be learned without removing the noise component as much as possible. Thus, a blood vessel image in which blurring has been suppressed can be output by generating an image using the learning model.

MODIFICATIONS

It should be understood that the embodiments disclosed here are examples in all respects and are not restrictive. The scope of the present invention is indicated by the appended claims rather than by the description of the above-described embodiments and includes all modifications (changes) within the meanings and the scopes equivalent to the scope of the claims.

Figure 9:
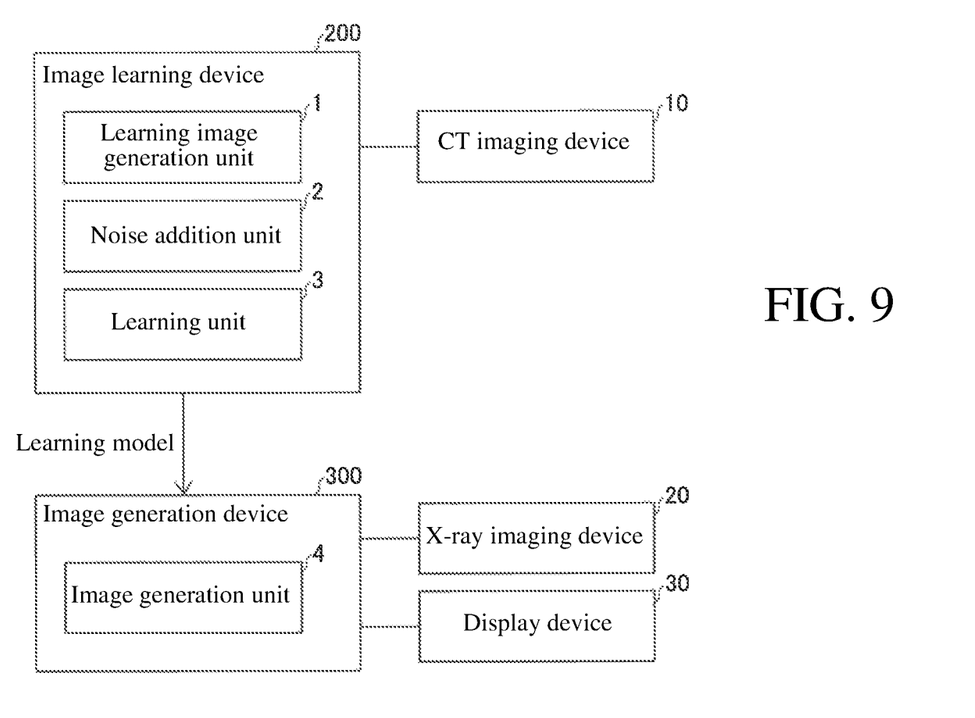
FIG. 9 is a diagram showing an image generation device according to a modification of an embodiment.

For example, in the above-described embodiment, an example has been shown in which the device for performing machine learning and the device for performing the image generation are the same device, but the present invention is not limited thereto. In the present invention, the device for performing the machine learning and the device for performing the image generation may be separate devices. For example, as shown in FIG. 9, the machine learning may be performed by the image learning device 200 provided with a learning image generation unit 1, a noise addition unit 2, and a learning unit 3. Further, the image generation may be performed by the image generation device 300 provided with an image generation unit 4. In this case, the image learning device 200 may be arranged at a location remote from the image generation device 300. Further, the image learning device 200 may be configured by a server computer provided on a cloud.

In the above-described embodiment, an example is shown in which it is configured such that the learning model for extracting or removing a specific portion from an imaging result of the X-ray imaging device is learned, but the present invention is not limited thereto. In the present invention, it may be configured to learn a learning model for extracting or removing a specific portion from an imaging result of an imaging device other than the X-ray imaging device. Further, the present invention may be widely and generally applied when the training output image at the time of learning is not a label image but an image of the same form as the training input image.

Further, in the above-described embodiment, an example is shown in which it is configured to generate an image from which the specific portion has been extracted or removed from the imaging result, but the present invention is not limited thereto. In the present invention, an image from which noise has been further removed may be generated from the image from which the specific portion has been extracted or removed.

Further, in the above-described embodiment, an example in which the subject is a person is shown, but the present invention is not limited thereto. In the present invention, the subject may be a living body other than a person or may be a non-living body.

Further, in the above-described embodiment, an example in which the specific portion is a blood vessel or a bone has been described, but the present invention is not limited thereto. In the present invention, the specific portion may be a portion other than a blood vessel and a bone.

Further, in the above-described embodiment, an example is shown in which the noise to be added to the training input image and the training output image is Gaussian noise, but the present invention is not limited thereto. In the present invention, the noise to be added to the training input image and the training output image may be noise other than Gaussian noise.

Further, in the above-described embodiment, for convenience of explanation, an example is shown in which the processing of the image generation device is described using a flow-driven flowchart in which processing is performed in the order along the processing flow, but the present invention is not limited thereto. In the present invention, the image generation device processing may be performed by event-driven processing that executes the processing on an event-by-event basis. In this case, the processing may be performed in a complete event-driven fashion or in combination of event-driven type processing and flow-driven type processing.

DESCRIPTION OF SYMBOLS

1: Learning image generation unit
2: Noise addition unit
3: Learning unit
4: Image generation unit
100: Image generation device
O: Subject

The invention claimed is:

1. An image generation device comprising:
a learning image generation unit configured to generate, based on three-dimensional data having three-dimensional pixel value data, a two-dimensional training input image in an area including a specific portion of a subject and a training output image that is an image showing the specific portion or an image excluding the specific portion at the same angle of view as the training input image;
a noise addition unit configured to add the same noise to the training input image and the training output image;
a learning unit configured to learn a learning model for extracting or removing the specific portion by performing machine learning based on the training input image to which the noise has been added and the training output image to which the noise has been added; and
an image generation unit configured to generate, from a captured image including the specific portion, an image from which the specific portion has been extracted or removed, using a learned learning model,
wherein the noise addition unit is configured to add noise adjusted based on noise of an imaging result that captured an image to the training input image and the training output image.

2. The image generation device as recited in claim 1, wherein the learning image generation unit is configured to acquire the three-dimensional data based on a computed tomography image that captured the subject and generate the training input image and the training output image by a digital reconstruction simulation.

3. The image generation device as recited in claim 1, wherein the noise addition unit is configured to add Gaussian noise and is configured to add Gaussian noise adjusted to a standard deviation corresponding to a standard deviation of noise of the imaging result that captured the image to the training input image and the training output image.

4. The image generation device as recited in claim 1, wherein the specific portion is a bone,
wherein the learning image generation unit is configured to generate a two-dimensional training input image in an area including a bone of the subject and the training output image excluding the bone of the subject,
wherein the learning unit is configured to learn the learning model for removing the bone by performing machine learning based on the training input image to which the noise has been added and the training output image to which the noise has been added, and
wherein the image generation unit is configured to generate, from the image including the imaged bone, an image from which the bone has been removed, using the learned learning model.

5. The image generation device as recited in claim 1, wherein the specific portion is a blood vessel,
wherein the learning image generation unit is configured to generate a two-dimensional training input image of an area including a blood vessel of the subject and the training output image indicating the blood vessel of the subject,
wherein the learning unit is configured to learn the learning model for extracting the blood vessel by performing machine learning, based on the training input image to which the noise has been added and the training output image to which the noise has been added, and
wherein the image generation unit is configured to generate, from an image including an imaged blood vessel, an image by extracting the blood vessel using the learned learning model.

6. An image generation method comprising:
generating a two-dimensional training input image in an area including a specific portion of a subject, based on three-dimensional data having three-dimensional pixel value data;
generating a training output image which is an image showing the specific portion or an image excluding the specific portion at the same angle of view as the training input image;
adding the same noise to the training input image and the training output image, the noise being noise adjusted based on noise of an imaging result that captured an image;
learning a learning model for extracting or removing the specific portion by performing machine learning based on the training input image to which the noise has been added and the training output image to which the noise has been added; and
generating an image from which the specific portion has been extracted or removed, from the captured image including the specific portion, using the learned learning model.

7. A method of producing a learned model, comprising:
generating a two-dimensional training input image in an area including the specific portion of a subject, based on three-dimensional data having three-dimensional pixel value data;
generating a training output image which is an image showing the specific portion or an image excluding the specific portion at the same angle of view as the training input image;
adding the same noise to the training input image and the training output image, the noise being noise adjusted based on noise of an imaging result that captured an image; and
learning a learning model for extracting or removing the specific portion by performing machine learning based on the training input image to which the noise has been added and the training output image to which the noise has been added.

* * * * *